US006248726B1

(12) United States Patent
Alsop et al.

(10) Patent No.: US 6,248,726 B1
(45) Date of Patent: Jun. 19, 2001

(54) METHOD OF PERITONEAL DIALYSIS USING GLUCOSE POLYMER SOLUTIONS

(75) Inventors: Ranulph Michael Alsop, Alderley Edge; Raymond Brian Forrester, Sandbach; David John Manning, Congleton, all of (GB)

(73) Assignee: M L Laboratories plc, London (GB)

( * ) Notice: Subject to any disclaimer, the term of this patent is extended or adjusted under 35 U.S.C. 154(b) by 0 days.

(21) Appl. No.: 07/954,686

(22) Filed: Sep. 30, 1992

Related U.S. Application Data

(63) Continuation of application No. 07/779,129, filed on Oct. 16, 1991, now abandoned, which is a continuation-in-part of application No. 06/875,461, filed on Jun. 18, 1996, now abandoned.

(30) Foreign Application Priority Data

Jun. 22, 1985 (GB) .......................................... BA85/15842

(51) Int. Cl.$^7$ .................................................... A61K 31/70
(52) U.S. Cl. .................................. 514/58; 514/54; 514/60
(58) Field of Search .................................... 514/58, 60, 54

(56) References Cited

U.S. PATENT DOCUMENTS 2,823,128 * 2/1958 Toulmin ................................ 536/112
4,182,756 * 1/1980 Ramsay et al. ........................ 536/1.1
4,357,323 * 11/1982 Soma et al. ............................ 536/1.1
4,514,560 * 4/1985 Shinohara et al. ..................... 536/1.1
4,886,789 * 12/1989 Milner ................................... 514/54

FOREIGN PATENT DOCUMENTS

| 0 153 164 | 8/1985 | (EP) . |
| WO 82/03329 | 10/1982 | (WO) . |

OTHER PUBLICATIONS

Alexander et al., Chemical Abstracts, vol. 98, 1983 No. 149608 K.*
Chemical Abstracts vol. 85, 1976, p. 410 (Reference No. 141580f).
Chemical Abstracts vol. 99, 1983, p. 619 (Reference No. 105608b).

* cited by examiner

*Primary Examiner*—Elli Peselev
(74) *Attorney, Agent, or Firm*—Marshall, O'Toole, Gerstein, Murray & Borun (57) ABSTRACT

There is described polysaccharides of high molecular weight for use in peritoneal dialysis. The polysaccharides are capable of dialysing human serum for long periods of time without causing damage to the peritoneum and are also capable of preventing loss of polymer from the peritoneum to the serum.

There is also described a method of making the polysaccharides and pharmaceutical formulations containing them.

4 Claims, 7 Drawing Sheets

Fig. 3.
ETHANOL FRACTIONATION

METHOD OF PERITONEAL DIALYSIS USING GLUCOSE POLYMER SOLUTIONS

This application is a continuation of application Ser. No. 07/779,129, filed Oct. 16, 1991, now abandoned, in turn a continuation of 06/875,461 filed Jun. 18, 1986, now abandoned.

This invention relates to a new form of polymer, a method for its production and compositions containing it.

Maltodextrins (glucose polymers) are produced by the hydrolysis of pure starch isolated from various natural products, e.g. wheat, rice, tapioca etc. In a typical process a pure isolated starch is produced by a multi-stage separation process involving removal of protein, oil, fibre and glutens before being hydrolysed.

As no single number can adequately characterise the molecular weight of a polymer, such as a maltodextrin, various averages are used. The most commonly used are the weight average molecular weight ($\overline{M}_w$) and the number average molecular weight ($\overline{M}_n$):

$$\overline{M}_w = \frac{\sum n_i M_i^2}{\sum n_i M_i}$$

$$\overline{M}_n = \frac{\sum n_i M_i}{\sum n_i}$$

where $n_i$ is the number of molecules of molecular weight $M_i$. $\overline{M}_w$ is particularly sensitive to changes in the high-molecular-weight content of the maltodextrin polymer whilst $\overline{M}_n$ is largely influenced by changes in the low molecular weight of the sample.

We have now found that it is possible to monitor starch hydrolysis and in particular to stop the hydrolytic action when the hydrolysate contains the maximum amount of molecules in the desired molecular weight range. The monitoring may be carried out by a technique known as size exclusion chromatography. Furthermore, fractionation of the starch hydrolysate can be monitored by size exclusion chromatography and a weight average molecular weight, a number average molecular weight and a molecular weight distribution of the products can be determined using chromatographic columns calibrated with dextran standards (Alsop et al Process Biochem 2 10–15 (1977) and Alsop et al J. Chromatography 246, 227–240, (1982)).

We have also found a method for optimising the yield of a glucose polymer with a preselected molecular weight range.

Glucose polymers are often characterised by the expression "degree of polymerisation" (DP). In this terminology a product may be described as having 20% of its weight comprising molecules with a DP greater than 10, ie. 20% has a molecular weight greater than 1656 (a polymer comprising 10 glucose units).

British Patent Application 2132914A describes a glucose polymer mixture having at least 15% by weight of glucose polymers of DP greater than 12 for use in continuous ambulatory peritoneal dialysis (CAPD). PCT/US Application 82/00774 describes a CAPD solution comprising glucose polymers of DP of at least 4.

European Patent Application 0076355 A2 discloses glucose polymer mixtures having at least 99% of glucose polymers of DP less than 12 for use in CAPD.

It has now surprisingly been found that certain polydisperse glucose polymer mixtures of high molecular weight are useful in medicine, e.g. in CAPD and in prevention of post-operative adhesions.

According to the invention we provide a glucose polymer mixture (I), wherein at least 50% by weight of the polymer is of molecular weight in the range 5000 to 30000.

We particularly prefer a glucose polymer (I), wherein at least 80% by weight of the polymer is of molecular weight in the range 5000 to 50,000.

We prefer the glucose polymer (I) to have a weight average molecular weight in the range of from 5000 to 100000, preferably of from 5000 to 50000, more preferably of from 12000 to 25000, and most preferably of from 14000 to 20000.

We prefer the glucose polymer (I) to have a number average molecular weight of less than 8000, preferably less than 5000, more preferably less than 4000 and most preferably less than 2900.

We prefer the content of mono-, di-, and tri-saccharide compounds present in the glucose polymer (I) to be less than 5% by weight, more preferably less than 2% and most preferably 0% by weight. By 0% we mean an amount which is undetectable by conventional methods.

We further prefer that the content of glucose polymers with molecular weight greater than 100000 in the glucose polymer (I) should be less than 5%, preferably less than 3% and most preferably less than 1% by weight.

We prefer the glucose polymers to be substantially free from endotoxins and nitrogenous contaminants arising from the original starch, or from the enzyme preparations used for its hydrolysis.

We particularly prefer the endotoxin level to be less than 0.25 endotoxin units/ml, more preferably less than 0.12 endotoxin units/ml and most preferably less than 0.06 endotoxin units/ml as determined by the Limulus Lysate Test (US Pharmacopoeia).

We prefer the nitrogen content of the glucose polymers to be less than 0.01% w/w, more preferably less than 0.001% w/w and most preferably zero as determined by the Kjeldahl method (British Pharmacopoeia)

We also prefer the glucose polymers to be substantially free of undesirable metals, e.g. aluminium. Thus we prefer the level of aluminium to be less than 500 ppb, more preferably less than 200 ppb and most preferably less than 100 ppb.

We also prefer an aqueous solution comprising 10% w/v of the glucose polymer to be substantially clear and colourless. Thus we prefer such a solution to have a turbidity value of less than 30 EEL units (US Pharmacopoeia), more preferably less than 20 EEL units and most preferably less than 10 EEL units. We also prefer such a solution to have no substantially visible colour. We particularly prefer the solution to have a visible colour of less than 10 APHA Hazen units and more preferably less than 5 APHA Hazen units. The content of colour precursors such as 5-hydroxymethyl furfural can be measured by absorption of ultraviolet light of wavelength 275 or 284 nm. We prefer the absorbance to be less than 0.5, more preferably less than 0.25 and most preferably less than 0.15. The transmission of ultraviolet light measured at a wavelength of 430 nm is preferably greater than 90% and more preferably greater than 95%.

It is a further feature of this invention to provide a glucose polymer (I) having up to 20% by weight of glucose polymers with a molecular weight of from 800 to 10,000, preferably of from 1500 to 4000. We particularly prefer a glucose polymer (I) having up to 20% by weight of glucose polymers with a molecular weight of from 1500 to 2500, more preferably up to 10% by weight and most preferably up to 7% by weight.

According to the invention we also provide a method for the production of a glucose polymer (I), which comprises a) fractional precipitation of an aqueous solution of a glucose polymer containing polymer (I) with a water miscible solvent, and/or b) filtration of an aqueous solution of a glucose polymer containing polymer (I) through membranes possessing an appropriate molecular weight cut-off range. The molecular weight cut-off range may be determined empirically.

In process a) the process parameters used are interdependent and each parameter may vary depending upon the desired quality of the product, the desired molecular weight range, etc. The water miscible solvent may be an alcohol, eg an alkanol, such as ethanol. The solvent may be present in an aqueous solution which is mixed with an aqueous glucose polymer. The concentration of the solvent in the aqueous solution before mixing may be from 60 to 100%v/v, preferably from 75 to 90%v/v, and most preferably about 85%v/v.

The concentration of the aqueous glucose polymer solution before mixing may be from 0 to 80% w/v, preferably from 15 to 65% w/v, and most preferably from 30 to 40% w/V.

The fractionation may be carried out at a temperature of from 10 to 40° C. and more preferably from 20 to 30° C.

In process b) the type of membrane material used may vary with the particular molecular weight distribution which is desired. A chemically inert plastics material may be used for the membrane, eg. a cellulose acetate or polytetrafluoroethylene. We particularly prefer to use a material which is mechanically stable at high temperatures and pressures, eg. a polysulphone.

A series of membranes may be used consecutively such that both a high and a low molecular weight fractionation is carried out. The membrane fractionation may be carried out at elevated temperature sufficient to prevent bacteriological contamination. We prefer the fractionation to be carried out at a temperature of from 0 to 90° C., preferably from 20 to 80° C., and most preferably from 65° to 75° C.

The feed solution may be of a concentration of from 1.0 to 30.0% w/v, preferably from 5 to 15% w/v and most preferably about 10% w/v.

The glucose polymer starting material is preferably prepared by a method, e.g. hydrolysis, designed to optimise the proportion of polymer (I), and the progress of that method is preferably monitored by size exclusion chromatography. Any starch may be used in the hydrolysis but we prefer to use a cornstarch.

The molecular weight distribution of the fractions may be determined using the chromatographic techniques described by Alsop et al J. Chromatography 246, 227–240 (1982). The optical rotation of the various solutions produced may also be used to identify the concentrations of the polymer contained by the solutions.

The high molecular weight waste products from the fractionations may be further hydrolysed to produce further quantities of lower molecular weight products which can be fractionated. The low molecular weight waste products may be useful in the production of glucose syrups.

Before, during and/or after the fractionation of process a) or b) the polymer may be purified. The purification may be to remove undesirable colour or to remove contaminants, for example proteins, bacteria, bacterial toxins, fibres or trace metals, eg aluminium. Any conventional purification technique may be applied, for example, filtration and/or absorption/adsorption techniques such as ion exchange or charcoal treatment.

The product of the fractionation of process a) or b) may be packaged and transported as a syrup or solution, for example an aqueous solution. However, we prefer the product to be in a solid form, preferably a powder, and most preferably spray dried granules.

The glucose polymer (I) is useful in a wide variety of medical indications, e.g. peritoneal dialysis, as a nutritional agent or for the prevention of post-operative adhesions etc.

According to the invention we also provide a pharmaceutical composition comprising a glucose polymer (I), wherein at least 50% of the polymer is of a molecular weight in the range 5000 to 30000, in admixture with a pharmaceutically acceptable adjuvant, diluent or carrier.

Any composition for use in CAPD preferably comprises physiologically acceptable electrolytes, eg. sodium, potassium, calcium and magnesium in order to prevent the transfer of desirable electrolytes from the serum to the peritoneum. The amounts may vary depending upon the requirements of any individual patient and are generally sufficient to provide an osmolarity of from about 240 to 275 mOsm/liter (see Example A).

According to the invention we also provide a physiologically acceptable polysaccharide (II) with an osmolarity of less than 160 mOsm/liter, preferably less than 110 mOsm/liter more preferably less than 90 mOsm/liter and most preferably less than 20 mOsm/liter, which is capable of being used in solution in the dialysis of normal human serum. By normal human serum we mean serum with an osmolarity of between 280 and 290 mOsm/liter at 37° C. The polysaccharide (II) preferably has the molecular weight and other parameters described above with respect to glucose polymer (I). Any suitable polysaccharide may be used but we prefer the polysaccharide to be a glucose polymer (I).

The polysaccharide (II) may be prepared by any of the processes hereinbefore described or by conventional processes known per se.

We also provide a composition capable of dialysing normal human serum comprising a polysaccharide (II) and having an osmolarity somewhat greater than normal serum. The osmolarity of the composition is preferably less than 400 mOsm/liter, more preferably less than 350 mOsm/liter and most preferably less than 330 mOsm/liter at 37° C. We particularly prefer a composition with an osmolarity less than 300 mOsm/liter at 37° C.

The composition may be in solid form, eg suitable for extemporaneous production of a solution, or it may be a liquid, eg in the form of an aqueous solution. The composition preferably includes pharmacologically acceptable electrolytes. Such electrolytes may include appropriate ions, eg of sodium, potassium, calcium, magnesium and chloride; buffers, eg. lactate, acetate or bisulphite; or other additives, such as amino acids, polyols or insulin.

The polymer (I) and the polysaccharide (II) are advantageous over the prior art. The long term use of high osmolarity glucose solutions in peritoneal dialysis can result in irreversible changes to the peritoneal membrane due to the continuous high pressure differentials across the peritoneum. When a glucose solution with a low osmolarity is used in CAPD for greater than four hours glucose may be lost from the peritoneum to the serum, this is undesirable, particularly in diabetic patients. The present invention provides a method of applying an osmotic pressure over the peritoneum for greater than four hours without causing damage to the peritoneum whilst preventing appreciable loss of polysaccharide to the serum from the peritoneum and maintaining the flow of water from the serum to the peritoneum.

BRIEF DESCRIPTION OF DRAWINGS

The invention will now be described by way of example only and by reference to the attached drawings in which.

In the Examples OR means optical rotations.

The molecular weight distribution of the starch hydrolysate starting material which was used in Examples 1 and 2 is shown in Table 1. The starting material was found to have an $\overline{M}_w$ of 6309 and an $\overline{M}_n$ of 401.

EXAMPLE 1

Ethanol Fractionation

Figure 1:
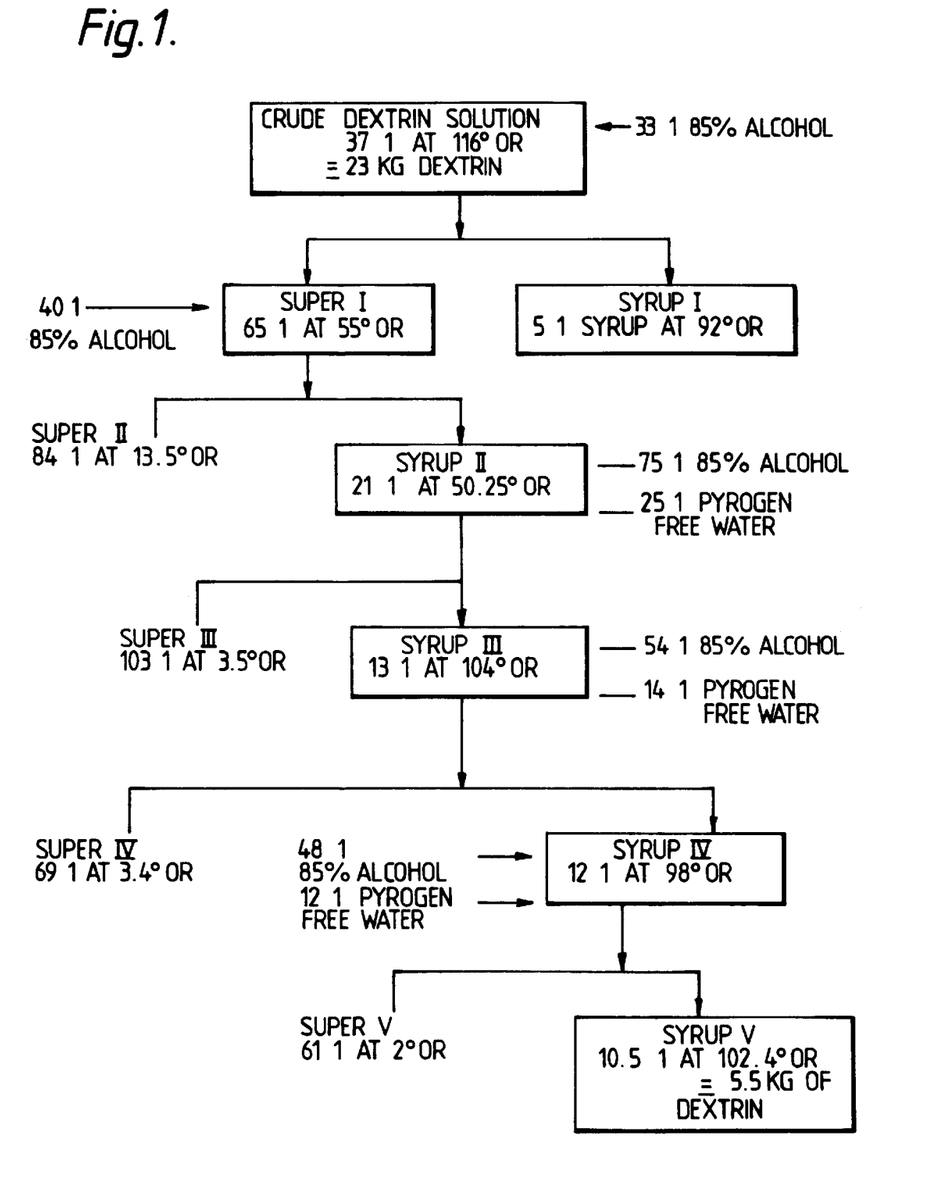
FIG. 1 is a flow diagram of the process described in Example 1.

The fractionation procedure used to isolate the required molecular weight distribution of a maltodextrin syrup is given in FIG. 1. The precise technique to be used will of course be varied to take account of the quality and molecular weight distribution of the maltodextrin used as the starting material.

Aqueous ethanol (33 l at 85%v/v) was added, with stirring, to 37 l of a maltodextrin syrup (at 116° OR=23 kg, dissolved maltodextrins). After settling the resulting Syrup I (5 l at 92° OR) was drawn from the bottom outlet of the fractionator.

Aqueous ethanol (40 l at 85% v/v) was added, with stirring, to the Supernatant I. After settling the Supernatant II (84 l at 13.5° OR) was decanted.

Aqueous ethanol (75 l at 85% v/v) and pyrogen free water (25 l) were added, with stirring, to the Syrup II (46 l at 50.25° OR ). After settling the Supernatant III (103 l at 3.5° OR ) was decanted.

Aqueous ethanol (54 l at 85% v/v) and pyrogen free water (14 l) were added, with stirring, to the resulting Syrup III (13 l at 104° OR ). After settling the Supernatant IV (69 l at 3.4° OR ) was decanted.

Aqueous ethanol (48 l at 85% v/v) and pyrogen free water (12 l) were added with stirring, to the resulting Syrup IV (12 l at 98° OR ). After settling the required maltodextrin fraction, Syrup V, (10.5 l at 102.4° OR =5.5 kg dissolved maltodextrins) was drawn off. This represents 23.9% recovery of the maltodextrins present in the initial syrup. 3.8 kg of Syrup V was dissolved in pyrogen free water (25 l) and refluxed with stirring in the presence of 0.4 kg of activated carbon (Norit UK, GSX grade). The carbon was removed by filtration and the resulting syrup was used to prepare peritoneal dialysis solutions.

The $\overline{M}_w$ of the product maltodextrin after carbon treatment was 18949 and the $\overline{M}_n$ was 6316. The molecular weight distribution is shown in Table 2, 61% of the product lies within the range 5000 to 30000.

EXAMPLE 2

Ethanol Fractionation

Figure 2:
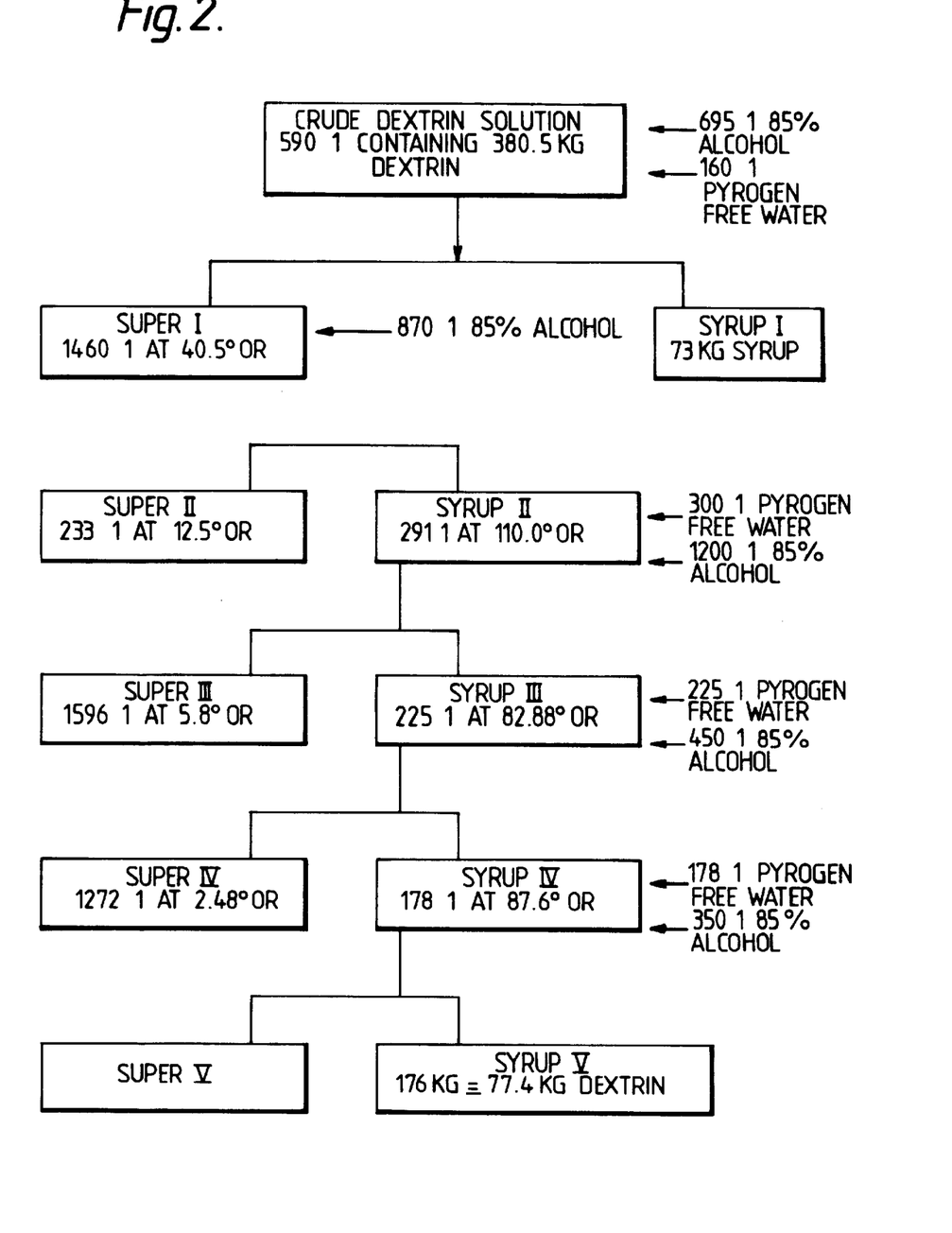
FIG. 2 is a flow diagram of the process described in Example 2.

The procedure of Example 1 was repeated using the quantities shown in FIG. 2. However, the carbon treatment was carried out by adding the activated carbon (Norit UK, grade GSX 5 kg) to the alcoholic Syrup V. The alcohol was removed by steam distillation and the carbon by depth filtration (Carlson Ford grade NA90). The resulting syrup was then spray dried.

The $\overline{M}_w$ of the product maltodextrin was 12027 and the $\overline{M}_n$ was 3447. The molecular weight distribution is shown in Table 3, 60% of the product lies within the range 5000 to 30000.

The $\overline{M}_w$ of the product maltodextrin after carbon treatment was 12027 and the $\overline{M}_n$ was 3447. The molecular weight distribution is shown in Table 3, 60% of the product lies within the range 5000 to 30000.

EXAMPLE 3

Ethanol Fractionation

The molecular weight distribution of the starting material is shown in Table 4. The starting material had an $\overline{M}_w$ of 11534 and an $\overline{M}_n$ of 586.

Figure 3:
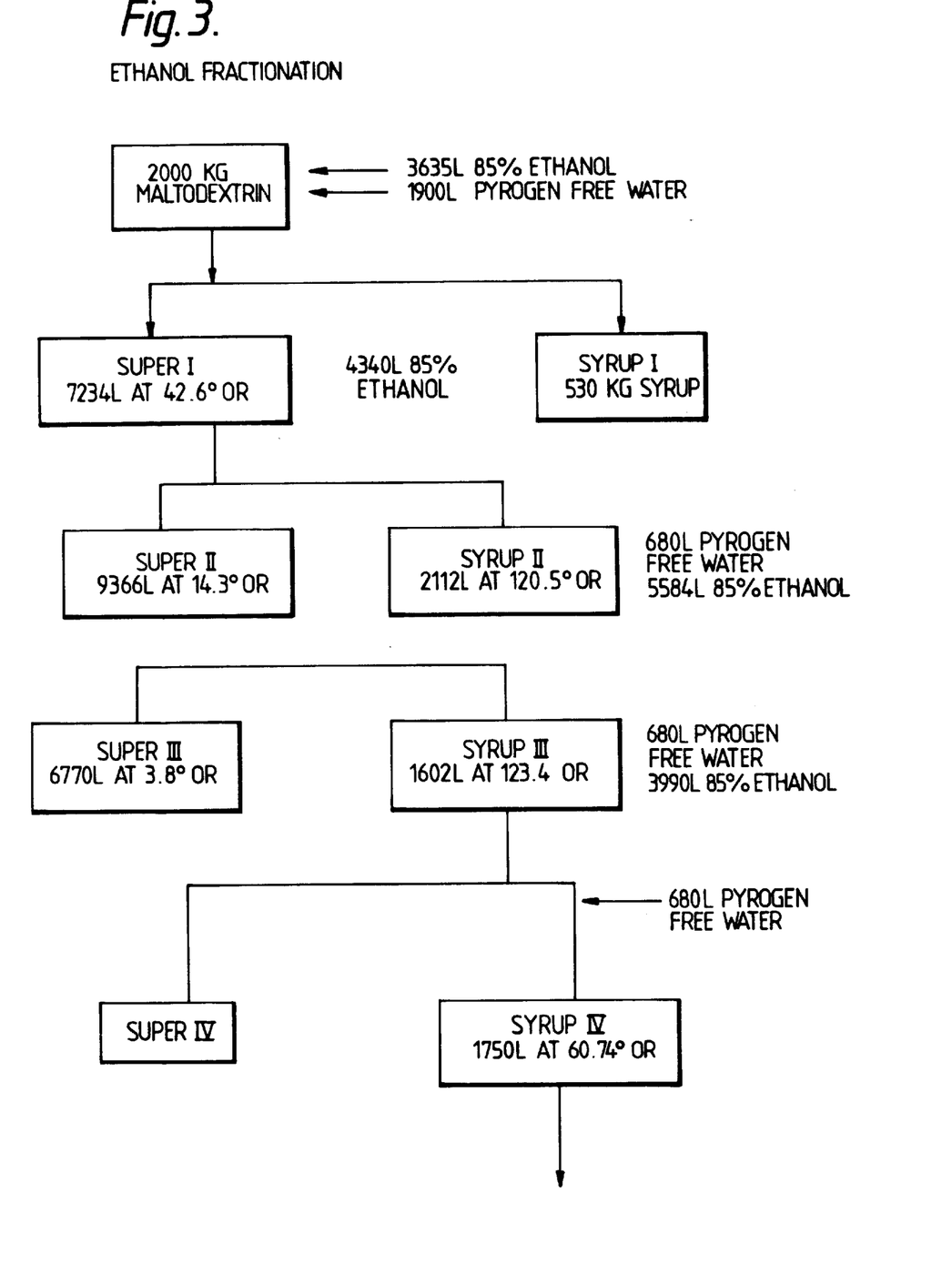
FIG. 3 is a flow diagram of the process described in Example 3.
Figure 4:
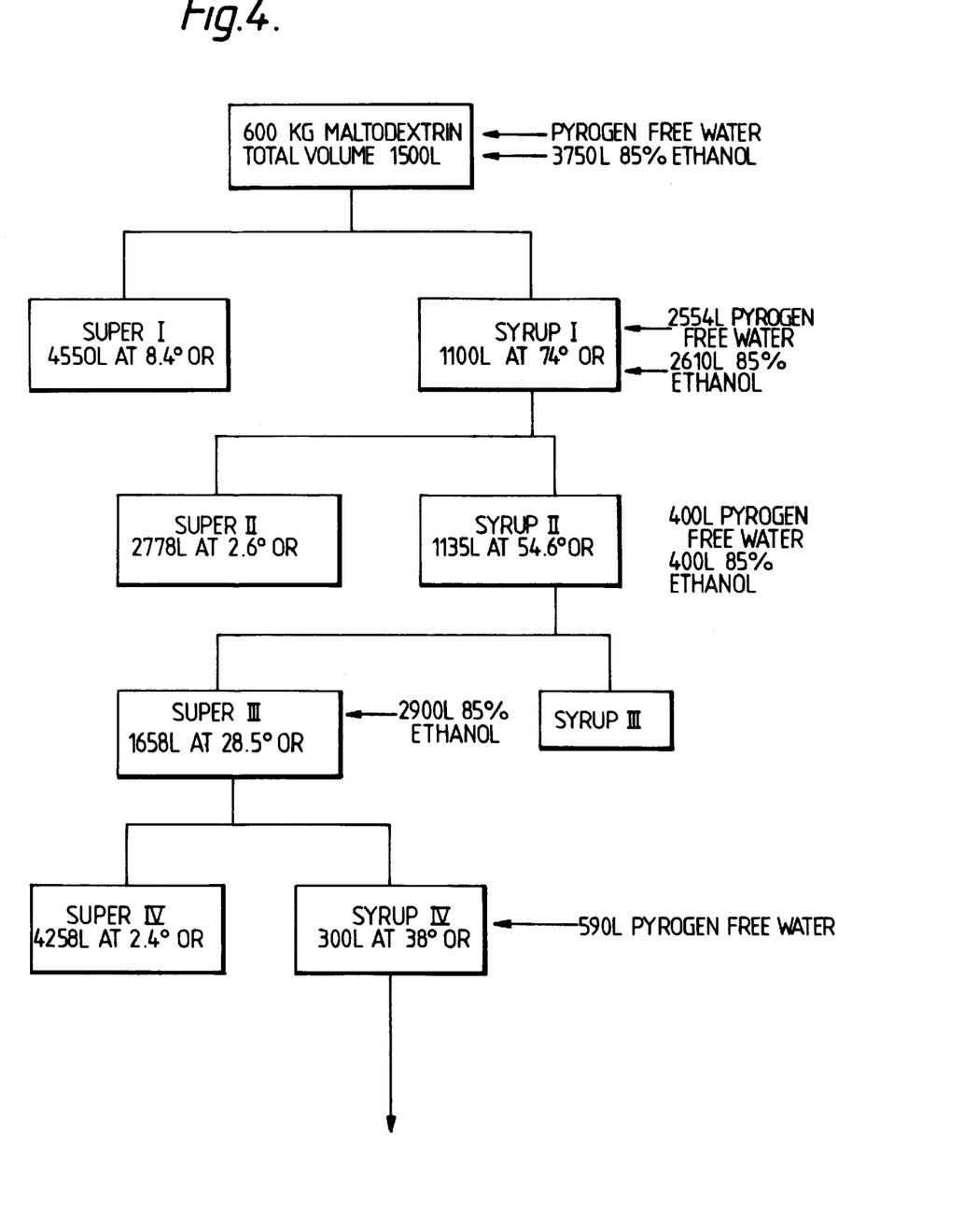
FIG. 4 is a flow diagram of the process described in Example 4.

The procedure of Example 1 was repeated using the quantities shown in FIG. 3. However, the carbon treatment was carried out by adding the activated carbon (Norit UK, Grade GSX 60 kg) to the alcoholic syrup IV. The activated carbon was filtered off by depth filtration (Carlson Ford Grade 'O' pads). A further carbon treatment was carried out on the syrup VI (15 kg Norit UK Grade GSX, filtered off using Carlson Ford Grade NA90 pads) during ethanol removal by steam distillation. The ethanol-free syrup was spray dried.

The $\overline{M}_w$ of the product maltodextrin was 21838 and the $\overline{M}_n$ was 7105. The molecular weight distribution is shown in Table 5, 58% of the product lies within the range 5000 to 30000.

EXAMPLE 4

Ethanol Fractionation

The molecular weight distribution of the starting material is shown in Table 6. The starting material had an $\overline{M}_w$ of 12636 and an $\overline{M}_n$ of 639.

Figure 5:
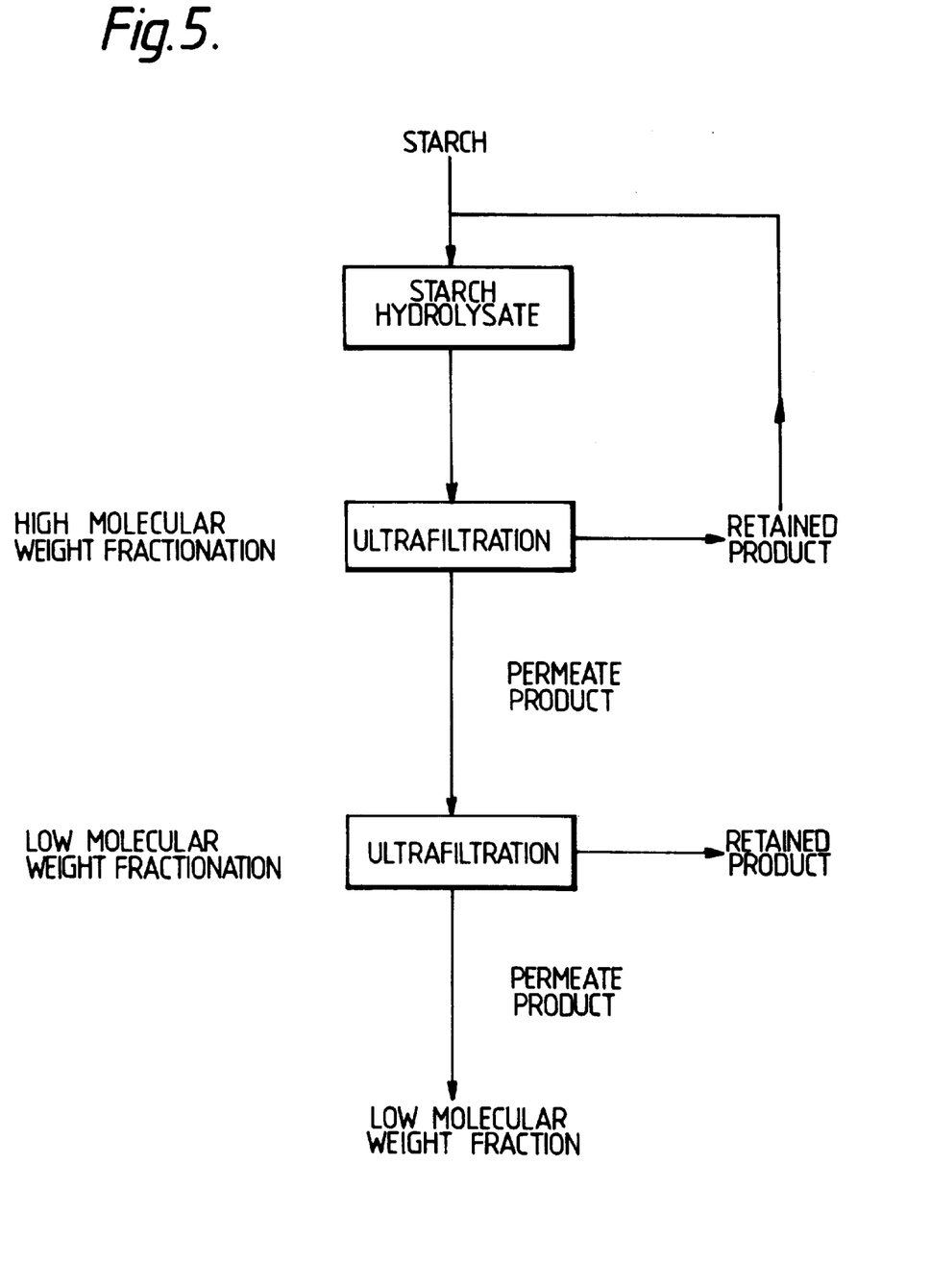
FIG. 5 is a flow diagram of the process described in Example 5.

The procedure of Example 1 was repeated using the quantities shown in FIG. 5. The carbon treatment was carried out by adding activated carbon (Norit UK, Grade GSX, 20 kg) to the alcoholic syrup IV. The carbon was filtered by depth filtration (Carlson Ford Grade 'O' pads). Ethanol was removed from the final syrup (syrup V) by steam distillation and the aqueous product ion exchanged (mixed bed system), and spray dried. The mixed bed resin was Duolite A1725 in the hydroxyl form and C225H in the chloride form. (Duolite is a trade mark).

The $\overline{M}_w$ of the product maltodextrin was 22020 and The $\overline{M}_n$ was 7767. The molecular weight distribution is shown in Table 7, 60% of the product lies within the range 5000 to 30000.

EXAMPLE 5

Membrane Fractionation a) A high molecular weight fractionation was carried out by passing 1.9 kg of starch hydrolysate, (molecular weight distribution, see Table 8), as a 10% w/v solution (20 liters) through a series of membranes. Polysulphone membranes with an approximate molecular weight cut-off of 20,000 and an area of 0.216 m² were used. The feed flowrate was 6.6 liters/min at a temperature of 70° C. The total solids level of the retained liquid was maintained at 10% w/v and the low molecular weight species were washed through the membrane. After 6.5 hours the concentration of carbohydrate in the permeate product stream leaving the ultrafiltration module was low, eg 0.5% w/v, (see Table 9) and the process was terminated. The high molecular weight residues were recovered from the membrane (0.2 kg, 10.5%) and the permeative low molecular weight product was isolated from the permeate (1.70 kg, 89.5%).

The molecular weight distribution of the product is shown in Table 10.

b) A low molecular weight fractionation was carried out by passing 0.64 kg of the low molecular weight product from Example 3a) as a 3.2% w/v solution (20 liters) through a series of membranes. Polysulphone membranes with an approximate molecular weight cut-off of 2,000 and an area S of 0.18 m² were used. The feed flowrate was 6.6 liters/min at a temperature of 70° C. The total solids level of the retained liquid was maintained at approximately 4.0% w/v and the low molecular weight species were washed through the membrane. After 95 minutes the concentration of carbohydrate in the permeate stream was zero (see Table 11) and the process was terminated. The undesired permeate product was recovered (0.465 kg, 73%) and the desired retained product was 0.166 kg (26%).

The molecular weight distribution of the product is shown in Table 12, 55% of the product lies within the range 5000 to 30000.

EXAMPLE 6 a) Membrane Fractionation

The procedure for Example 5a) was repeated using 2.0 kg of starch hydrolysate. Membranes were used with a cut-off value of 25000 an area of 0.144 m². After 5.5 hours the concentration of the carbohydrate in the permeate was undetectable (see Table 13). The high molecular weight residues were recovered from the membrane (0.384 kg, 19.2%) and the permeative low molecular weight product was isolated from the permeate (1.613 kg, 80.6%). The molecular weight distribution of the permeate is given in Table 14. $\overline{M}_w$ was found to be 4906 and $\overline{M}_n$ determined as 744.

b) Ethanol Fractionation 1.7 kg of maltodextrin from Example 6a) in 53 liters of pyrogen free water was mixed with 132.5 liters of aqueous ethanol (85% v/v).

The syrup from the fractionation had an $\overline{M}_w$ of 19712 and an $\overline{M}_n$ of 4798. The molecular weight distribution is shown in Table 15, 55% of the product lies within the range 5000 to 30000.

EXAMPLE 7

Ethanol Fractionation

The procedure of Example 3 was carried out. Syrup V was isolated and the molecular weight distribution determined.

The $\overline{M}_w$ of the product maltodextrin was 20211 and the $\overline{M}_n$ was 2890. The molecular weight distribution is shown in Table 16, 50% of the product lies within the range 5000 to 30000.

EXAMPLE A

Two examples of peritoneal dialysis solutions are shown below. The ionic electrolytes behave ideally and therefore 1 mOsm/l is equivalent to 1 mmol/l.

|  | 1 | 2 |
|---|---|---|
| Sodium (mO sm/1) | 131 | 138 |
| Potassium (mO sm/1) | 0 | 0 |
| Calcium (mO sm/1) | 1.8 | 1.78 |
| Magnesium (mO sm/1) | 0.75 | 0.75 |
| Chloride (mO sm/1) | 91 | 90 |
| Lactate (mO sm/1) | 45 | 45 |
| Acetate (mO sm/1) | — | — |
| Bisulphite (mO sm/1) | — | — |
| Total Electrolyte Osmolarity (mO sm/1) | 269.6 | 275.5 |
| Glucose polymer (I) (mO sm/1) | 12.9 | 12.9 |
|  | (50 g/l) | (50 g/l) |
| Total Osmolarity | 282.5 | 288.4 |

TABLE 1

Molecular Weight Distribution

| MOLECULAR WEIGHTS | INTEGRAL DISTRIBUTION |
|---|---|
| 165 | 0.00 |
| 167 | 2.50 |
| 172 | 5.00 |
| 178 | 7.50 |
| 184 | 10.00 |
| 191 | 12.50 |
| 199 | 15.00 |
| 207 | 17.50 |
| 216 | 20.00 |
| 226 | 22.50 |
| 237 | 25.00 |
| 249 | 27.50 |
| 262 | 30.00 |
| 276 | 32.50 |
| 291 | 35.00 |
| 307 | 37.50 |
| 326 | 40.00 |
| 346 | 42.50 |
| 366 | 45.00 |
| 391 | 47.50 |
| 419 | 50.00 |
| 446 | 52.50 |
| 488 | 55.00 |
| 532 | 57.50 |
| 598 | 60.00 |
| 681 | 62.50 |
| 837 | 65.00 |
| 1099 | 67.50 |
| 1570 | 70.00 |
| 2328 | 72.50 |
| 3436 | 75.00 |
| 4915 | 77.50 |
| 6789 | 80.00 |
| 7135 | 82.50 |
| 12074 | 85.00 |
| 13825 | 87.50 |
| 20735 | 90.00 |
| 27447 | 92.50 |
| 37044 | 95.00 |
| 53463 | 97.50 |
| 199559 | 100.00 |

TABLE 2

Molecular Weight Distribution

| MOLECULAR WEIGHTS | INTEGRAL DISTRIBUTION |
|---|---|
| 296 | 0.00 |
| 1231 | 2.50 |
| 1756 | 5.00 |
| 2279 | 7.50 |
| 2795 | 10.00 |
| 3291 | 12.50 |
| 3771 | 15.00 |
| 4246 | 17.50 |
| 4722 | 20.00 |
| 5203 | 22.50 |
| 5696 | 25.00 |
| 6196 | 27.50 |
| 6718 | 30.00 |
| 7247 | 32.50 |
| 7809 | 35.00 |
| 8378 | 37.50 |
| 8986 | 40.00 |
| 9607 | 42.50 |
| 10272 | 45.00 |
| 10960 | 47.50 |
| 11695 | 50.00 |
| 12472 | 52.50 |
| 13295 | 55.00 |
| 14184 | 57.50 |
| 15126 | 60.00 |
| 16162 | 62.50 |
| 17274 | 65.00 |
| 18499 | 67.50 |
| 19872 | 70.00 |
| 21352 | 72.50 |
| 23122 | 75.00 |
| 25084 | 77.50 |
| 27319 | 80.00 |
| 30070 | 82.50 |
| 33400 | 85.00 |
| 37527 | 87.50 |
| 42867 | 90.00 |
| 50412 | 92.50 |
| 61686 | 95.00 |
| 82648 | 97.50 |
| 288182 | 100.00 |

TABLE 3

Molecular Weight Distribution

| MOLECULAR WEIGHTS | INTEGRAL DISTRIBUTION |
|---|---|
| 183 | 0.00 |
| 484 | 2.50 |
| 874 | 5.00 |
| 1292 | 7.50 |
| 1695 | 10.00 |
| 2082 | 12.50 |
| 2460 | 15.00 |
| 2836 | 17.50 |
| 3215 | 20.00 |
| 3595 | 22.50 |
| 3986 | 25.00 |
| 4382 | 27.50 |
| 4786 | 30.00 |
| 5204 | 32.50 |
| 5627 | 35.00 |
| 6072 | 37.50 |
| 6519 | 40.00 |
| 6994 | 42.50 |
| 7473 | 45.00 |
| 7982 | 47.50 |
| 8499 | 50.00 |
| 9048 | 52.50 |
| 9611 | 55.00 |
| 10212 | 57.50 |
| 10836 | 60.00 |
| 11502 | 62.50 |
| 12208 | 65.00 |
| 12955 | 67.50 |
| 13777 | 70.00 |
| 14637 | 72.50 |
| 15626 | 75.00 |
| 16708 | 77.50 |
| 17905 | 80.00 |
| 19298 | 82.50 |
| 20957 | 85.00 |
| 22960 | 87.50 |
| 25476 | 90.00 |
| 29002 | 92.50 |
| 34287 | 95.00 |
| 44550 | 97.50 |
| 299523 | 100.00 |

TABLE 4

Molecular Weight Distribution

| MOLECULAR WEIGHTS | INTEGRAL DISTRIBUTION |
|---|---|
| 146 | 0.00 |
| 157 | 2.50 |
| 173 | 5.00 |
| 192 | 7.50 |
| 213 | 10.00 |
| 235 | 12.50 |
| 259 | 15.00 |
| 285 | 17.50 |
| 313 | 20.00 |
| 343 | 22.50 |
| 378 | 25.00 |
| 411 | 27.50 |
| 450 | 30.00 |
| 489 | 32.50 |
| 536 | 35.00 |
| 583 | 37.50 |
| 636 | 40.00 |
| 695 | 42.50 |
| 755 | 45.00 |
| 837 | 47.50 |
| 920 | 50.00 |
| 1036 | 52.50 |
| 1161 | 55.00 |
| 1350 | 57.50 |
| 1590 | 60.00 |
| 1919 | 62.50 |
| 2393 | 65.00 |
| 3094 | 67.50 |
| 4176 | 70.00 |
| 5731 | 75.00 |
| 7802 | 75.00 |
| 10354 | 77.50 |
| 13393 | 80.00 |
| 17014 | 82.50 |
| 21436 | 85.00 |
| 27030 | 87.50 |
| 34348 | 90.00 |
| 44586 | 92.50 |
| 60087 | 95.00 |
| 89965 | 97.50 |
| 578156 | 100.00 |

TABLE 5

Molecular Weight Distribution

| MOLECULAR WEIGHTS | INTEGRAL DISTRIBUTION |
|---|---|
| 1394 | 2.50 |
| 2060 | 5.00 |
| 2644 | 7.50 |
| 3199 | 10.00 |
| 3751 | 12.50 |
| 4299 | 15.00 |
| 4856 | 17.50 |
| 5421 | 20.00 |
| 6003 | 22.50 |
| 6597 | 25.00 |
| 7208 | 27.50 |
| 7841 | 30.00 |
| 8497 | 32.50 |
| 9175 | 35.00 |
| 9881 | 37.50 |
| 10615 | 40.00 |
| 11385 | 42.50 |
| 12189 | 45.00 |
| 13033 | 47.50 |
| 13924 | 50.00 |
| 14870 | 52.50 |
| 15874 | 55.00 |
| 16947 | 57.50 |
| 18096 | 60.00 |
| 19333 | 62.50 |
| 20685 | 65.00 |
| 22167 | 67.50 |
| 23793 | 70.00 |
| 25616 | 72.50 |
| 27661 | 75.00 |
| 29973 | 77.50 |
| 32624 | 80.00 |
| 35745 | 82.50 |
| 39445 | 85.00 |
| 44003 | 87.50 |
| 49720 | 90.00 |
| 57401 | 92.50 |
| 68831 | 95.00 |
| 90432 | 97.50 |

TABLE 6

Molecular Weight Distribution

| MOLECULAR WEIGHTS | INTEGRAL DISTRIBUTION |
|---|---|
| 146 | 0.00 |
| 156 | 2.50 |
| 175 | 5.00 |
| 197 | 7.50 |
| 223 | 10.00 |
| 250 | 12.50 |
| 279 | 15.00 |
| 311 | 17.50 |
| 345 | 20.00 |
| 381 | 22.50 |
| 420 | 25.00 |
| 462 | 27.50 |
| 506 | 30.00 |
| 555 | 32.50 |
| 603 | 35.00 |
| 662 | 37.50 |
| 721 | 40.00 |
| 792 | 42.50 |
| 875 | 45.00 |
| 971 | 47.50 |
| 1099 | 50.00 |
| 1269 | 52.50 |
| 1496 | 55.00 |
| 1827 | 57.50 |
| 2320 | 60.00 |
| 3043 | 62.50 |
| 4107 | 65.00 |
| 5556 | 67.50 |
| 7396 | 70.00 |
| 9581 | 75.00 |
| 12065 | 75.00 |
| 14880 | 77.50 |
| 18153 | 80.00 |
| 21986 | 82.50 |
| 26590 | 85.00 |
| 32293 | 87.50 |
| 39532 | 90.00 |
| 49285 | 92.50 |
| 63509 | 95.00 |
| 89961 | 97.50 |
| 439968 | 100.00 |

TABLE 7

Molecular Weight Distribution

| MOLECULAR WEIGHTS | INTEGRAL DISTRIBUTION |
|---|---|
| 1586 | 2.50 |
| 2290 | 5.00 |
| 2882 | 7.50 |
| 3443 | 10.00 |
| 3991 | 12.50 |
| 4545 | 15.00 |
| 5110 | 17.50 |
| 5694 | 20.00 |
| 6302 | 22.50 |
| 6931 | 25.00 |
| 7587 | 27.50 |
| 8263 | 30.00 |
| 8965 | 32.50 |
| 9692 | 35.00 |
| 10441 | 37.50 |
| 11218 | 40.00 |
| 12030 | 42.50 |
| 12878 | 45.00 |
| 13761 | 47.50 |
| 14691 | 50.00 |
| 15671 | 52.50 |
| 16705 | 55.00 |
| 17805 | 57.50 |
| 18982 | 60.00 |
| 20244 | 62.50 |
| 21615 | 65.00 |
| 23120 | 67.50 |
| 24766 | 70.00 |
| 26584 | 72.50 |
| 28624 | 75.00 |
| 30930 | 77.50 |
| 33568 | 80.00 |
| 36623 | 82.50 |
| 40240 | 85.00 |
| 44626 | 87.50 |
| 50148 | 90.00 |
| 57346 | 92.50 |
| 67788 | 95.00 |
| 86399 | 97.50 |

TABLE 8

Starch Hydrolysate
Molecular Weight Distribution

| MOLECULAR WEIGHTS | INTEGRAL DISTRIBUTION |
|---|---|
| 146 | 0.00 |
| 160 | 2.50 |
| 176 | 5.00 |
| 195 | 7.50 |
| 217 | 10.00 |
| 240 | 12.50 |
| 264 | 15.00 |
| 291 | 17.50 |
| 322 | 20.00 |
| 354 | 22.50 |
| 390 | 25.00 |
| 428 | 27.50 |
| 470 | 30.00 |
| 511 | 32.50 |
| 558 | 35.00 |
| 605 | 37.50 |
| 657 | 40.00 |
| 714 | 42.50 |
| 772 | 45.00 |
| 852 | 47.50 |
| 934 | 50.00 |
| 1050 | 52.50 |
| 1185 | 55.00 |
| 1398 | 57.50 |
| 1688 | 60.00 |
| 2104 | 62.50 |
| 2708 | 65.00 |
| 3617 | 67.50 |
| 4870 | 70.00 |
| 6517 | 75.00 |
| 8552 | 75.00 |
| 10946 | 77.50 |
| 13729 | 80.00 |
| 17036 | 82.50 |
| 21022 | 85.00 |
| 25964 | 87.50 |
| 32324 | 90.00 |
| 40911 | 92.50 |
| 53516 | 95.00 |
| 76329 | 97.50 |
| 356145 | 100.00 |

TABLE 9

| Time | Pressure in Bar | Pressure out Bar | Temp ° C. | Permeate Flow Rate l/min | Feed Soln Concn % w/v | Permeate Conc % w/v |
|---|---|---|---|---|---|---|
| 0 | 4.6 | 3.4 | 64 | on total recycle | | |
| 1 | " | " | 64 | 190 | 10.5 | 7 |
| 1.5 | " | " | 68 | 192 | 10 | 6.5 |
| 2 | " | " | 71 | 198 | 9 | 5 |
| 3 | " | " | 69 | 166 | 8 | 3.5 |
| 4 | " | " | 69 | 165 | 6.75 | 2.25 |
| 6 | " | " | 70 | 148 | 6 | 1 |
| 6.5 | " | " | 65 | 140 | 8 | 0.5 |

TABLE 10

Permeate (Ex 5(a))
Molecular Weight Distribution

| MOLECULAR WEIGHTS | INTEGRAL DISTRIBUTION |
|---|---|
| 146 | 0.00 |
| 169 | 2.50 |
| 205 | 5.00 |
| 247 | 7.50 |
| 285 | 10.00 |
| 323 | 12.50 |
| 362 | 15.00 |
| 403 | 17.50 |
| 444 | 20.00 |
| 488 | 22.50 |
| 533 | 25.00 |
| 581 | 27.50 |
| 630 | 30.00 |
| 681 | 32.50 |
| 734 | 35.00 |
| 787 | 37.50 |
| 845 | 40.00 |
| 906 | 42.50 |
| 966 | 45.00 |
| 1038 | 47.50 |
| 1117 | 50.00 |
| 1196 | 52.50 |
| 1303 | 55.00 |
| 1423 | 57.50 |
| 1567 | 60.00 |
| 1758 | 62.50 |
| 2003 | 65.00 |
| 2308 | 67.50 |
| 2720 | 70.00 |
| 3287 | 72.50 |
| 4080 | 75.00 |
| 5156 | 77.50 |
| 6535 | 80.00 |
| 8280 | 82.50 |
| 10326 | 85.00 |
| 12731 | 87.50 |
| 15631 | 90.00 |
| 19283 | 92.50 |
| 24378 | 95.00 |
| 32986 | 97.50 |
| 93587 | 100.00 |

TABLE 11

| Time | Pressure in Bar | Pressure out Bar | Temp ° C. | Permeate Flow Rate l/min | Feed Soln Concn % w/v | Permeate Conc %. w/v |
|---|---|---|---|---|---|---|
| 0 | 5.4 | 4.6 | 70 | 390 | 3.25 | 1.75 |
| 15 mins | 5.4 | 4.6 | 70 | 400 | 3.5 | 1.5 |
| 35 mins | 5.4 | 4.6 | 71 | 300 | 5.0 | 2.0 |
| 60 mins | 5.4 | 4.6 | 70 | 280 | 4.25 | 1 |
| 95 mins | 5.4 | 4.6 | 69 | 280 | 3.0 | 0 |

TABLE 12

Retentate (Ex 5(b))
Molecular Weight Distribution

| MOLECULAR WEIGHTS | INTEGRAL DISTRIBUTION |
|---|---|
| 186 | 0.00 |
| 834 | 2.50 |
| 1339 | 5.00 |
| 1837 | 7.50 |
| 2410 | 10.00 |
| 3090 | 12.50 |
| 3869 | 15.00 |

TABLE 12-continued

Retentate (Ex 5(b))
Molecular Weight Distribution

| MOLECULAR WEIGHTS | INTEGRAL DISTRIBUTION |
|---|---|
| 4717 | 17.50 |
| 5613 | 20.00 |
| 6540 | 22.50 |
| 7492 | 25.00 |
| 8458 | 27.50 |
| 9433 | 30.00 |
| 10414 | 32.50 |
| 11398 | 35.00 |
| 12385 | 37.50 |
| 13374 | 40.00 |
| 14384 | 42.50 |
| 15406 | 45.00 |
| 16449 | 47.50 |
| 17519 | 50.00 |
| 18611 | 52.50 |
| 19754 | 55.00 |
| 20917 | 57.50 |
| 22167 | 60.00 |
| 23437 | 62.50 |
| 24832 | 65.00 |
| 26283 | 67.50 |
| 27852 | 70.00 |
| 29576 | 72.50 |
| 31415 | 75.00 |
| 33457 | 77.50 |
| 35747 | 80.00 |
| 38449 | 82.50 |
| 41731 | 85.00 |
| 45703 | 87.50 |
| 50765 | 90.00 |
| 57945 | 92.50 |
| 69100 | 95.00 |
| 90766 | 97.50 |
| 410452 | 100.00 |

TABLE 13

| Time | Pressure in Bar | Pressure out Bar | Temp °C. | Permeate Flow Rate 1/min | Feed Soln Concn % w/v | Permeate Conc % w/v |
|---|---|---|---|---|---|---|
| 0.75 | 4.7 | 3.3 | 67 | 225 | 9.5 | 5.0 |
| 1.25 | 4.7 | 3.8 | 68 | 184 | 10.5 | 5.5 |
| 2.50 | 4.8 | 3.2 | 70 | 150 | 9.0 | 4.0 |
| 3.50 | 4.8 | 3.2 | 70 | 144 | 8.0 | 1.5 |
| 4.50 | 4.8 | 3.2 | 69 | 130 | 6.5 | 0.5 |
| 5.50 | 4.8 | 3.2 | 69 | 123 | 6.0 | 0 |

TABLE 14

Permeate (Ex 6)
Molecular Weight Distribution

| MOLECULAR WEIGHTS | INTEGRAL DISTRIBUTION |
|---|---|
| 146 | 0.00 |
| 170 | 2.50 |
| 207 | 5.00 |
| 251 | 7.50 |
| 293 | 10.00 |
| 335 | 12.50 |
| 378 | 15.00 |
| 423 | 17.50 |
| 469 | 20.00 |
| 516 | 22.50 |
| 566 | 25.00 |
| 616 | 27.50 |
| 660 | 30.00 |
| 720 | 32.50 |
| 773 | 35.00 |
| 827 | 37.50 |
| 882 | 40.00 |
| 939 | 42.50 |
| 1004 | 45.00 |
| 1070 | 47.50 |
| 1135 | 50.00 |
| 1226 | 52.50 |
| 1320 | 55.00 |
| 1418 | 57.50 |
| 1567 | 60.00 |
| 1717 | 62.50 |
| 1947 | 65.00 |
| 2218 | 67.50 |
| 2566 | 70.00 |
| 3056 | 72.50 |
| 3718 | 75.00 |
| 4671 | 77.50 |
| 5959 | 80.00 |
| 7656 | 82.50 |
| 9753 | 85.00 |
| 12271 | 87.50 |
| 15332 | 90.00 |
| 19237 | 92.50 |
| 24688 | 95.00 |
| 34400 | 97.50 |
| 98105 | 100.00 |

TABLE 15

Molecular Weight Distribution

| MOLECULAR WEIGHTS | INTEGRAL DISTRIBUTION |
|---|---|
| 170 | 0.00 |
| 845 | 2.50 |
| 1292 | 5.00 |
| 1674 | 7.50 |
| 2044 | 10.00 |
| 2429 | 12.50 |
| 2841 | 15.00 |
| 3283 | 17.50 |
| 3754 | 20.00 |
| 4269 | 22.50 |
| 4805 | 25.00 |
| 5361 | 27.50 |
| 5958 | 30.00 |
| 6583 | 32.50 |
| 7232 | 35.00 |
| 7937 | 37.50 |
| 8666 | 40.00 |
| 9447 | 42.50 |
| 10273 | 45.00 |
| 11129 | 47.50 |
| 12062 | 50.00 |
| 13024 | 52.50 |
| 14053 | 55.00 |
| 15147 | 57.50 |
| 16281 | 60.00 |
| 17537 | 62.50 |
| 18860 | 65.00 |
| 20264 | 67.50 |
| 21839 | 70.00 |
| 23542 | 72.50 |
| 25408 | 75.00 |
| 27488 | 77.50 |

TABLE 15-continued

Molecular Weight Distribution

| MOLECULAR WEIGHTS | INTEGRAL DISTRIBUTION |
|---|---|
| 29900 | 80.00 |
| 32694 | 82.50 |
| 36020 | 85.00 |
| 40183 | 87.50 |
| 45419 | 90.00 |
| 52731 | 92.50 |
| 64063 | 95.00 |
| 85249 | 97.50 |
| 349210 | 100.00 |

TABLE 16

Molecular Weight Distribution

| MOLECULAR WEIGHTS | INTEGRAL DISTRIBUTION |
|---|---|
| 147 | 0.00 |
| 354 | 2.50 |
| 627 | 5.00 |
| 918 | 7.50 |
| 1243 | 10.00 |
| 1602 | 12.50 |
| 1996 | 15.00 |
| 2431 | 17.50 |
| 2908 | 20.00 |
| 3428 | 22.50 |
| 3990 | 25.00 |
| 4591 | 27.50 |
| 5232 | 30.00 |
| 5924 | 32.50 |
| 6653 | 35.00 |
| 7417 | 37.50 |
| 8230 | 40.00 |
| 9092 | 42.50 |
| 9990 | 45.00 |
| 10946 | 47.50 |
| 11966 | 50.00 |
| 13032 | 52.50 |
| 14178 | 55.00 |
| 15407 | 57.50 |
| 16704 | 60.00 |

TABLE 16-continued

Molecular Weight Distribution

| MOLECULAR WEIGHTS | INTEGRAL DISTRIBUTION |
|---|---|
| 18105 | 62.50 |
| 19643 | 65.00 |
| 21999 | 67.50 |
| 23093 | 70.00 |
| 25087 | 72.50 |
| 27332 | 75.00 |
| 29844 | 77.50 |
| 32692 | 80.00 |
| 35966 | 82.50 |
| 39805 | 85.00 |
| 44449 | 87.50 |
| 50079 | 90.00 |
| 57437 | 92.50 |
| 67881 | 95.00 |
| 86087 | 97.50 |
| 331467 | 100.00 |

We claim:

1. A method of treatment of a human requiring dialysis of the serum by use of an aqueous solution of a physiologically acceptable mixture of glucose polymers derived from the hydrolysis of starch, wherein at least 50% by weight of said mixture comprises polymers having molecular weights in the range of from 5,000 to 30,000, and wherein said mixture has a weight average molecular weight of from 5,000 to 50,000, and a number average molecular weight of from 2,890 to 8,000.

2. A method of treatment in accordance with claim 1 wherein up to 20% by weight of the polymers in the mixture have a molecular weight of from 800 to 10,000.

3. A method of treatment in accordance with claim 1 wherein the mixture contains less than 5% by weight of glucose polymers with molecular weight greater than 100,000.

4. A method of claim 1 wherein the aqueous solution further comprises amino acids.

* * * * *